United States Patent [19]
Pommer et al.

[11] 3,994,909
[45] Nov. 30, 1976

[54] 1,2,4-OXADIAZOLIN-5-ONE DERIVATIVES

[75] Inventors: Ernst-Heinrich Pommer, Limburgerhof; Helmut Hagen; Helmut Fleig, both of Frankenthal, all of Germany

[73] Assignee: BASF Aktiengesellschaft, Ludwigshafen (Rhine), Germany

[22] Filed: Jan. 16, 1975

[21] Appl. No.: 541,650

[30] Foreign Application Priority Data
Feb. 5, 1974 Germany............................ 2405324

[52] U.S. Cl. ..................... 260/302D; 260/302 SD; 260/307 A; 424/270; 424/272
[51] Int. Cl.$^2$......................................... C07D 285/08
[58] Field of Search....... 260/307 A, 302 D, 302 SD

[56] References Cited
UNITED STATES PATENTS
3,326,931  6/1967  Narayanan et al.................. 260/307

OTHER PUBLICATIONS
D'Alo et al. — C. A. 65, 18576 g (1966).

*Primary Examiner*—Raymond V. Rush
*Attorney, Agent, or Firm*—Johnston, Keil, Thompson & Shurtleff

[57] ABSTRACT
1,2,4-oxidiazolin-5-one derivatives having a good fungicidal action. Fungicidal compounds of one of the formulae:

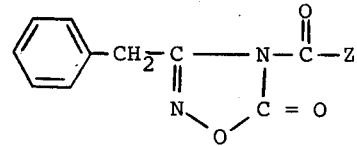

wherein Z is —OCH$_3$, —OC$_2$H$_5$, —OCH(CH$_3$)$_{NH(CH}$, —$_{NHC2}$H$_5$ or —NH(lH$_2$)$_3$CH$_3$;

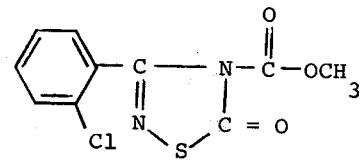

or

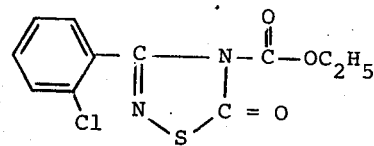

7 Claims, No Drawings

1,2,4-OXADIAZOLIN-5-ONE DERIVATIVES

The present invention relates to new and valuable 1,2,4-oxadiazolin-5-one derivatives having a good fungicidal action, a process for their production, fungicides containing these compounds, and their use as fungicides.

It is known to use zinc ethylenebisdithiocarbamate and wettable sulfur as fungicides. However, their action is insufficient.

We have now found that 1,2,4-oxadiazolin-5-one derivatives of the formula

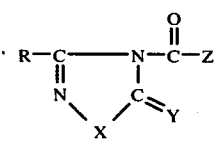

where R denotes linear or branched $C_1$ to $C_{20}$, and preferably $C_1$ to $C_4$, alkyl which is unsubstituted or substituted by F, Cl, Br, $NO_2$, $C_1$ to $C_4$ dialkylamino, $C_1$ to $C_4$ acylamino and $C_1$ to $C_4$ alkoxy, R further denotes aralkyl, or aryl which is unsubstituted or substituted by one or more of the abovementioned substituents or $C_1$ to $C_4$ alkyl, X denotes oxygen or sulfur, Y denotes oxygen or sulfur, and Z denotes amino, $C_1$ to $C_4$ alkylamino, $C_1$ to $C_4$ dialkylamino or $C_1$ to $C_4$ alkoxy, have a good fungicidal action.

The new compounds may be prepared for example by reacting the starting materials of the formula

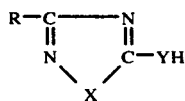

where R, X and Y have the above meanings, in the presence of an acid-binding agent, either undiluted or — preferably — in the presence of an inert organic solvent, with the equivalent amount or an excess of a chloroformic acid derivative of the formula

Z having the above meanings, at a temperature of from 0° to 140° C, and preferably 20° to 100° C. The reaction takes from 1 to 20, and preferably 2 to 5, hours. Suitable acid-binding agents, which are expediently used in a stoichiometric ratio with reference to starting material II, are alkali metal carbonates such as $Na_2CO_3$ and $K_2CO_3$, and tertiary amines such as pyridine and triethylamine. Examples of inert organic solvents are halohydrocarbons, e.g., $CH_2Cl_2$ and $CHCl_3$, carboxamides such as dimethylformamide and dimethyl acetamide, and ethers such as tetrahydrofuran and dioxane. The reaction may be carried out at atmospheric or superatmospheric pressure. Instead of the abovementioned acid-binding agents, the alkali metal salts of starting materials II may be used, the reaction conditions being otherwise the same. The sodium salts of II are for instance obtained by concentrating a methanolic solution of sodium methylate and an equivalent amount of II.

The process may for instance be carried out in accordance with the following equation:

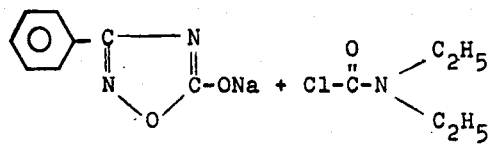

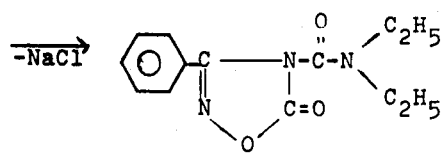

Where, in formula I, X and Y each denote oxygen and R denotes amino or alkylamino, it is also possible to react cyanic acid or a $C_1$ to $C_4$ alkyl isocyanate with starting material II (X and Y being oxygen) in an organic solvent in the presence of a tertiary amine, e.g., triethylamine and pyridine, at temperatures of from 0° to 60° C, and preferably 20° to 40° C. The isocyanate may, with reference to starting material II, be used in stoichiometric amounts or in excess. Examples of suitable organic solvents are chlorohydrocarbons such as $CH_2Cl_2$ and $CHCl_3$, carboxamides such as dimethylformamide and dimethyl acetamide, and ethers such as tetrahydrofuran and dioxane; generally, there is used per mole of II (X and Y = O) 500 ml of solvent — it is however also possible to use a medium of greater or lesser concentration. The amount of tertiary amine which is added is from 0.01 to 0.1, and preferably from 0.02 to 0.04, mole per 0.1 mole of starting material II.

Employing 3-phenyl-5-hydroxy-1,2,4-oxadiazole and ethyl isocyanate for illustration purposes, the reaction may be represented by the following equation:

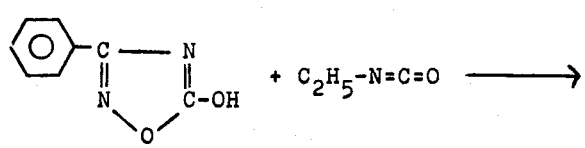

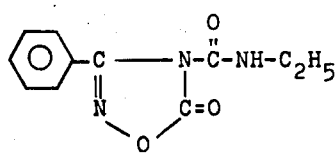

Some of the starting materials II are disclosed in the literature, and new ones were prepared by known processes. Methods for producing starting materials II are discussed in A. Weissberger, The Chemistry of Heterocyclic Compounds, Five- and Six-Membered Compounds with Nitrogen and Oxygen, Interscience Publishers, New York, 255–256, 1962, and in Helv. chim. Acta, 47, 838–848, 1964, with regard to 5-mercapto- and 5-hydroxy-1,2,4-oxadiazoles, and in Chem. Ber., 90, 182–187, 1957, with regard to 5-mercapto- and 5-hydroxy-1,2,4-thiadiazoles. Examples of suitable starting materials II are as follows: 3-methyl-5-hydroxy-1,2,4-oxadiazole, 3-ethyl-5-hydroxy-1,2,4-thiadiazole, 3-n-propyl-5-mercapto-1,2,4-oxadiazole, 3-sec-butyl-5-hydroxy-1,2,4-oxadiazole, 3-n-undecyl-5-mercapto-1,2,4-thiadiazole, 3-(isopropoxymethyl)-5-hydroxy-1,2,4-oxadiazole, 3-(2-N,N-diethylaminoethyl)-5-hydroxy-1,2,4-thiadiazole, 3-chloromethyl-5-mercapto-1,2,4-oxadiazole, 3-(2-phenylethyl)-5-mercapto-1,2,4-thiadiazole, 3-phenyl-5-mercapto-1,2,4-oxadiazole, 3-(3-chlorophenyl)-5-hydroxy-1,2,4-oxadiazole, 3-(4-chloro-2-methylphenyl)-5-hydroxy-1,2,4-thiadiazole, 3-(4-nitrophenyl)-5-mercapto-1,2,4-oxadiazole, 3-(4-trifluoromethylphenyl)-5-mercapto-1,2,4-thiadiazole.

The following are examples of suitable starting materials III: methyl chloroformate, isopropyl chloroformate, sec-butyl chloroformate, dimethylcarbamyl chloride, and diethylcarbamyl chloride; methyl isocyanate, ethyl isocyanate, isopropyl isocyanate and n-butyl isocyanate are examples of alkyl isocyanates.

Numerous reactions of hydroxy or mercapto compounds with chloroformic acid derivatives or isocyanates have been described, e.g., Houben-Weyl-Mueller, Meth. Org. Chem., VIII, 105 et seq., 1952; IX, 804 et seq., 1955.

However, according to Lyell C. Behr in The Chemistry of Heterocyclic Compounds (loc. cit.), 5-hydroxy-1,2,4-oxadiazoles do not react with typical hydroxyl reagents such as $PCl_5$, $POCl_3$ and phenyl isocyanate. It is therefore surprising that the new compounds may be obtained by the methods described above.

The preparation of compounds I according to the invention is illustrated in more detail by the following examples, in which parts are by weight. They bear the same relation to parts by volume as kilograms to liters. The melting points have not been corrected.

EXAMPLE 1

3-benzyl-4-isopropoxycarbonyl-1,2,4-oxadiazolin-5-one

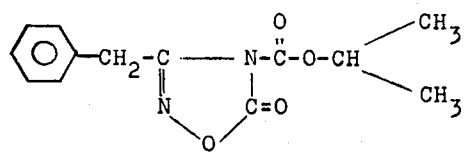

17.6 parts of 3-benzyl-5-hydroxy-1,2,4-oxadiazole, 6.9 parts of potassium carbonate and 12.3 parts of isopropyl chloroformate are heated for 5 hours at 60° C. After the mixture has cooled, the precipitated potassium chloride is removed by suction filtration and the filtrate concentrated. The residue is recrystallized from n-propanol. There is obtained 15.5 parts (59% of theory) of the desired product; m.p.: 80° C.

EXAMPLE 2

3-benzyl-4-ethoxycarbonyl-1,2,4-oxadiazolin-5-one

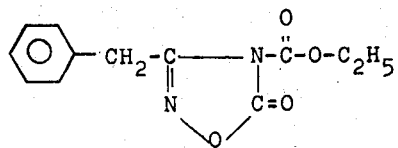

17.6 parts of 3-benzyl-5-hydroxy-1,2,4-oxadiazole in 100 parts of methanol is added to 5.6 parts of sodium methylate. The solvent is distilled off, 50 parts of ethyl chloroformate is added to the residue, and the reaction mixture is heated for 2 hours at 95° C. The excess chloroformate is distilled off and the mixture is boiled in ligroin and filtered hot. After cooling there is obtained 18.5 parts (75% of theory) of the desired product; m.p.: 129° C.

EXAMPLE 3

3-phenyl-[4-N,N-dimethylcarbamyl]-1,2,4-oxadiazolin-5-one

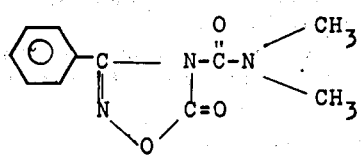

18.4 parts of the sodium salt of 3-phenyl-5-hydroxy-1,2,4-oxadiazole and 50 parts of dimethylcarbamyl chloride are heated for 2 hours at 100° C. After the mixture has cooled it is poured onto ice. The product which precipitates is washed with water and dried. The melting point is 110° C, and the yield 15.5 parts (67% of theory).

EXAMPLE 4

3-(2-chlorophenyl)-(4-N,N-dimethylcarbamyl)-1,2,4-thiadiazolin-5-one

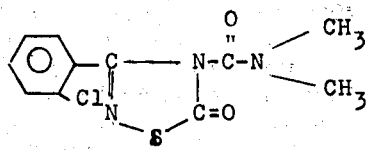

23.5 parts of the sodium salt of 3-(2-chlorophenyl)-5-hydroxy-1,2,4-thiadiazole and 12 parts of dimethylcarbamyl chloride in 100 parts of dioxane are heated for 5 hours at 50° C. After the mixture has cooled the precipitated sodium chloride is removed by suction filtration and the filtrate concentrated. The precipitated solid is recrystallized from n-propanol. The product melts at 126° C, and the yield is 17 parts (60% of theory).

EXAMPLE 5

3-(4-methylphenyl)-4-N,N-dimethylcarbamyl-1,2,4-thiadiazoline-5-thione

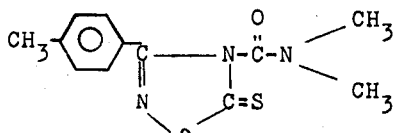

23 parts of the sodium salt of 3-(4-methylphenyl)-5-mercapto-1,2,4-thiadiazole and 15 parts of dimethylcarbamyl chloride in 200 parts of dioxane are heated for 5 hours at reflux temperature. The solvent is distilled off, the precipitated solid is washed with water, and the residue recrystallized from alcohol. There is obtained 17.5 parts (63% of theory) of crystals of the desired product; m.p.: 178° C.

EXAMPLE 6

3-ethyl-4-N-methylcarbamyl-1,2,4-oxadiazolin-5-one

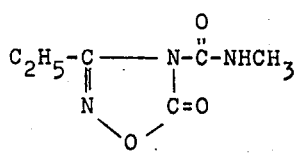

11.4 parts of 3-ethyl-5-hydroxy-1,2,4-oxadiazole (m.p.: 69° C) is stirred for 2 hours at room temperature with 6.5 parts of methyl isocyanate and 4 parts of triethylamine in 100 parts of dioxane. The reaction mixture is then poured into ice water, and the precipitated solid is suction filtered and rinsed with water. There is obtained 10.5 parts (61% yield) of the above compound; m.p.: 82° C.

EXAMPLE 7

3-benzyl-4-N-n-propylcarbamyl-1,2,4-oxadiazolin-5-one

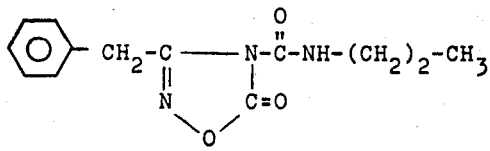

8.8 parts of 3-benzyl-5-hydroxy-1,2,4-oxadiazole is stirred for 1 hour at room temperature with 4.3 parts of n-propyl isocyanate and 2 parts of triethylamine in 50 parts of dioxane. The reaction mixture is then poured into ice water, and the precipitated solid is suction filtered and recrystallized from alcohol. There is obtained 8.5 parts (65% of theory) of the desired product; m.p.: 74° C.

The following compounds were obtained analogously:

| Compounds of the formula I | | | | m.p. [° C] |
|---|---|---|---|---|
| R | X | Y | Z | |
| $CH_3-$ | O | O | $-\overset{O}{\overset{\|}{C}}NHCH_3$ | 82–83 |
| $i-C_3H_7$ | O | O | $-\overset{O}{\overset{\|}{C}}-NHCH_3$ | 42–43 |
| $C_6H_{11}-CH_2-$ | O | O | $-\overset{O}{\overset{\|}{C}}-NHCH_3$ | 121 |
| $C_6H_{11}-CH_2-$ | O | O | $-\overset{O}{\overset{\|}{C}}-NHC_2H_5$ | 97 |
| $C_6H_{11}-CH_2-$ | O | O | $-\overset{O}{\overset{\|}{C}}-NH(CH_2)_3CH_3$ | 72 |
| $C_6H_{11}-CH_2-$ | O | O | $-\overset{O}{\overset{\|}{C}}-O-CH_3$ | 162 |
| $C_6H_{11}-CH_2-$ | O | O | $-\overset{O}{\overset{\|}{C}}-O-C_2H_5$ | 129 |
| $C_6H_{11}-$ | O | O | $-\overset{O}{\overset{\|}{C}}-O-C_2H_5$ | 72 |
| $C_6H_{11}-$ | O | O | $-\overset{O}{\overset{\|}{C}}-NH-CH_3$ | 120 |
| $C_6H_{11}-$ | O | O | $-\overset{O}{\overset{\|}{C}}-N\begin{smallmatrix}C_2H_5\\C_2H_5\end{smallmatrix}$ | 106 |
| $NO_2$-substituted cyclohexyl | O | O | $-\overset{O}{\overset{\|}{C}}-NH-CH_3$ | 152 |
| $CH_3,CH_3$-disubstituted cyclohexyl | O | O | $-\overset{O}{\overset{\|}{C}}-NHCH_3$ | 120 |
| $C_6H_{11}-$ | S | O | $-\overset{O}{\overset{\|}{C}}-N\begin{smallmatrix}CH_3\\CH_3\end{smallmatrix}$ | 170 |
| Cl-substituted cyclohexyl | S | O | $-\overset{O}{\overset{\|}{C}}-O-CH_3$ | 94 |
| Cl-substituted cyclohexyl | S | O | $-\overset{O}{\overset{\|}{C}}-O-C_2H_5$ | 86 |
| Cl,CH$_3$-disubstituted cyclohexyl | S | O | $-\overset{O}{\overset{\|}{C}}-N\begin{smallmatrix}CH_3\\CH_3\end{smallmatrix}$ | 146 |
| $C_6H_{11}-$ | S | S | $-\overset{O}{\overset{\|}{C}}-O-C_2H_5$ | 86 |
| $C_6H_{11}-$ | S | S | $-\overset{O}{\overset{\|}{C}}-N\begin{smallmatrix}CH_3\\CH_3\end{smallmatrix}$ | 151 |

Compounds of the formula I

| R | X | Y | Z | m.p. [° C] |
|---|---|---|---|---|
|  | S | S | —C(=O)—O—CH₃ | 70 |
|  | S | S | —C(=O)—O—C₂H₅ | 42 |
|  | S | S | —C(=O)—N(CH₃)₂ | 117 |
|  | S | S | —C(=O)—O—C₂H₅ | 78 |
|  | S | S | —C(=O)—N(N)(CH₃)(CH₃) | 134 |

The new compounds have a fungicidal action on numerous fungi. They are suitable for controlling fungi such as *Pythium ultimum*, *Phytophthora parasitica*, *Plasmopara viticola*, *Pseudoperonospora humuli*, *Aspergillus niger*, *Erysiphe graminis*, *Erysiphe cichoriacearum*, *Rhizoctonia solani*, *Pellicularia sasakii* and *Fusarium spec.*, and may be used in for instance the following crops: tomatoes, potatoes, grapes, hops, strawberries, wheat, barley, melons, cucumbers, groundnuts, soybeans, and cotton.

The active ingredients may also be mixed with other known fungicides, this often resulting in a broadening of the fungicidal spectrum. In some of these fungicidal compositions synergism is apparent, i.e., the fungicidal action of the composition is greater than that of the sum of the actions of its individual components. The following active ingredients have proved to be particularly suitable for these combinations:

N-trichloromethylthiophthalimide
N-trichloromethylthiotetrahydrophthalimide
N-(1,1,2,2-tetrachloroethylthio)-tetrahydrophthalimide
N,N-dimethyl-N'-phenyl-(N-fluorodichloromethylthio)-sulfamide
zinc-N,N'-ethylene-bis-(dithiocarbamate)
manganese (II)-N,N'-ethylene-bis-(dithiocarbamate)
manganese-zinc ethylene-bis(dithiocarbamate)
zinc-(N,N'-propylene-1,2-bis-(dithiocarbamate)
ammonia complex of zinc-(N,N'-ethylene-bis-dithiocarbamate) and
N,N'-polyethylene-bis-(thiocarbamoyl)-disulfide
ammonia complex of zinc-(N,N'-propylene-bis-dithiocarbamate) and
N,N'-polypropylene-bis-(thiocarbamoyl)-disulfide
bis-(dimethylthiocarbamoyl)-disulfide
2-ethylamino-4-hydroxy-5-butyl-6-methylpyrimidine
2,3-dihydro-6-methyl-1,4-oxathiin-5-carboxanilide
N-tridecyl-2,6-dimethylmorpholine
3,5-dimethyltetrahydro-1,3,5-thiadiazinethione-(2)
2,5-dimethylfuran-3-carboxanilide
2,5-dimethylfuran-3-carboxylic acid cyclohexylamide
2-iodobenzoic acid anilide
o-toluic acid anilide
diisopropyl-5-nitroisophthalate
2-(thiocyanomethylthio)-benzothiazole
1,2-bis-(3-methoxycarbonyl-2-thioureido)-benzene
2-methoxycarbonylaminobenzimidazole
methyl 1-(butylcarbamoyl)-2-benzimidazolecarbamate If necessary, these agents may be added to the fungicides of the invention immediately before use. The ratio by weight of art compound to active ingredient of the invention is from 1:10 to 10:1.

Application may be effected for instance in the form of directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, etc. and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silica gel, silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90% by weight of active ingredient.

The amount used of the agents according to the invention may vary and depends in essence on the type of effect to be achieved; it is generally from 0.1 to 15 (and more), preferably from 0.2 to 6, kg per hectare of active ingredient.

EXAMPLE 8

Delintered cotton seeds of the "Delta Pine" variety are thoroughly dusted with 0.3 g per 100 g of seed of a dressing consisting of an intimate mixture of 40% (by weight) of the active ingredient and 60% of talc. The seeds treated in this manner are placed in pots and covered with soil which has been previously artificially infected with the fungus Rhizoctonia solani. After 21 days the number of diseased plants is assessed and the results are compared with the untreated control and an art fungicide.

| Active ingredient | Diseased cotton plants in % |
|---|---|
| (cyclohexyl-CH₂-C(=N-O)-N(C=O)-C-O-CH₃ structure) | 0 |
| tetramethylthiuram disulfide (comparative agent) | 25 |
| control (untreated) | 100 |

EXAMPLE 9

The active ingredients are added to a nutrient solution ideally suited for promoting the growth of the fungus Aspergillus niger in amounts ranging from 50 to 250 parts (by weight) per million parts of solution. 20 mls of each solution treated in this manner is placed in Erlenmeyer flasks and inoculated with 0.3 mg of Aspergillus spores. The flasks are kept at 36° C for 120 hours, after which period the extent of fungus spread — predominantly on the surface of the nutrient solution — is assessed.

The figures in the table have the following meanings:
0 = no fungus growth, graduated down to
5 = uncontrolled fungus growth (surface of nutrient solution completely covered by fungus)

| Active ingredient | Amount of active ingredient in nutrient solution in ppm | | |
|---|---|---|---|
|  | 50 | 100 | 250 |
| (phenyl-CH₂-C(=N-O)-N(C=O)-C-O-C₂H₅ structure) | 2 | 2 | 0 |
| (phenyl-CH₂-C(=N-O)-N(C=O)-C-O-CH(CH₃)₂ structure) | 2 | 2 | 0 |
| (2-Cl-phenyl-C(=N-O)-N(C=O)-S-C-O-CH₃ structure) | 2 | 1 | 0 |
| (2-Cl-phenyl-C(=N-O)-N(C=O)-S-C-O-C₂H₅ structure) | 2 | 2 | 0 |
| control (untreated) | | | 5 |

EXAMPLE 10

Leaves of barley seedlings grown in pots are sprayed with aqueous emulsions consisting of 80% of active ingredient and 20% of emulsifier, and are dusted, after the sprayed layer has dried, with spores of barley mildew (*Erysiphe graminis*). The plants are then placed in a greenhouse at a temperature of from 20° to 22° C and a relative humidity of from 75 to 80%. The extent of fungus spread is assessed after 7 and 14 days. The length of time for which the action lasts is important as it indicates how often the plants to be protected have to be sprayed during the vegetation period to keep them free from fungus attack.

| Active ingredient | Amount of active ingredient in spray liquor (in wt%) | No. of days after which action was assessed (plants treated once) | |
|---|---|---|---|
| | | 7 | 14 |
| 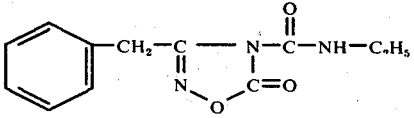 | 0.2 | 0 | 0 |
| | 0.1 | 0 | 1 |
| 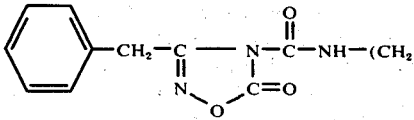 | 0.2 | 0 | 0 |
| | 0.1 | 0 | 2 |
| wettable sulfur (comparative agent) | 0.2 | 0 | 2 |
| | 0.1 | 1 | 3 |
| control (untreated) | — | 5 | 5 |

0 = no damage, graduated down to
5 = leaves completely covered by fungus

EXAMPLE 11

Leaves of potted vines of the Mueller-Thurgau variety are sprayed with aqueous dispersions consisting of 80% (by weight) of active ingredient and 20% of sodium lignin sulfonate (dry basis). 0.12% spray liquors (dry basis) are used. After the sprayed layer has dried, the leaves are infected with a zoospore suspension of *Plasmopara viticola*. The plants are first placed in a steam-saturated chamber at 20° C for 16 hours, and then moved to a greenhouse kept at from 20° to 30° C for 8 days. Finally the plants are again placed in the moist chamber for 16 hours to accelerate and intensify spore discharge from the sporangia. The number of spore sites on the undersides of the leaves is then counted. Untreated infected plants are used as control.

| Active ingredient | Attacked leaves in % |
|---|---|
| 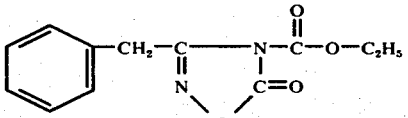 | 0 |
| 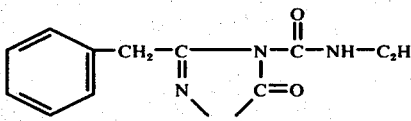 | 3 |
| 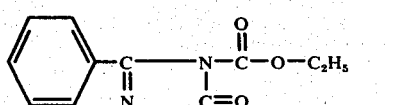 | 2 |
| zinc ethylenebisdithiocarbamate (comparative agent) | 19 |
| control (untreated) | 71 |

EXAMPLE 12

Tomato leaves are sprayed with aqueous dispersions consisting of 80% (by weight) of active ingredient and 20% of sodium lignin sulfonate (dry basis). 0.12% spray liquors (dry basis) are used. After the sprayed layer has dried, the leaves are infected with a zoospore suspension of the fungus Phytophthora infestans. The plants are then placed for 5 days in steam-saturated chamber at 16° C. After this time the untreated control plants have been attacked to the extent of from 80 to 100%.

| Leaf attack: | | |
|---|---|---|
| 0% | = | 0 |
| 1–5% | = | 1 |
| 6–20% | = | 2 |
| 21–50% | = | 3 |
| 51–85% | = | 4 |
| 86–100% | = | 5 |

| Active ingredient | Attack |
|---|---|
| 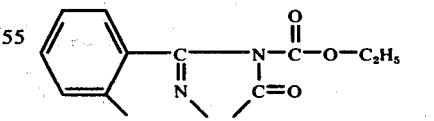 | 0 |
| 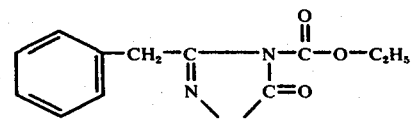 | 0 |
| zinc ethylenebisdithiocarbamate (comparative agent) | 2 |
| control (untreated) | 5 |

EXAMPLE 13

90 parts by weight of the compound of Example 1 is mixed with 10 parts by weight of N-methyl-α-pyrrolidone. A mixture is obtained which is suitable for application in the form of very fine drops.

EXAMPLE 14

20 parts by weight of the compound of Example 2 is dissolved in a mixture consisting of 80 parts by weight of xylene, 10 parts by weight of the adduct of 8 to 10 moles of ethylene oxide to 1 mole of oleic acid N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 15

20 parts by weight of the compound of Example 3 is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 16

20 parts by weight of the compound of Example 4 is dissolved in a mixture consisting of 25 parts by weight of cyclohexanol, 65 parts by weight of a mineral oil fraction having a boiling point between 210° and 280° C, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 17

20 parts by weight of the compound of Example 5 is well mixed with 3 parts by weight of the sodium salt of diisobutylnaphthalene-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE 18

3 parts by weight of the compound of Example 6 is intimately mixed with 97 parts by weight of particulate kaolin. A dust is obtained containing 3% by weight of the active ingredient.

EXAMPLE 19

30 parts by weight of the compound of Example 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

We claim:

1. A compound of the formula

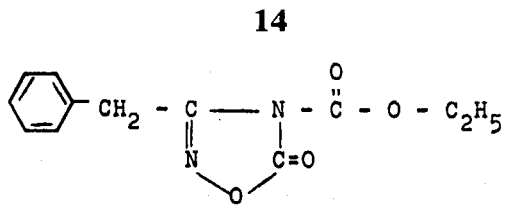

2. A compound of the formula

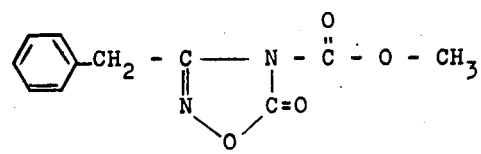

3. A compound of the formula

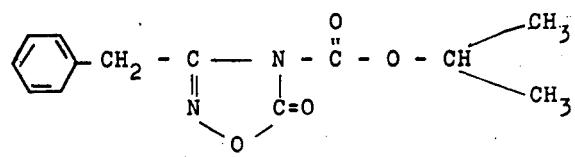

4. A compound of the formula

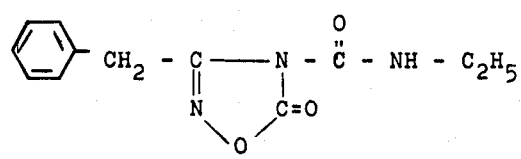

5. A compound of the formula

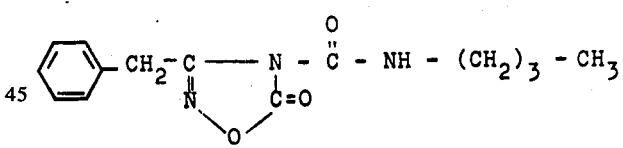

6. A compound of the formula

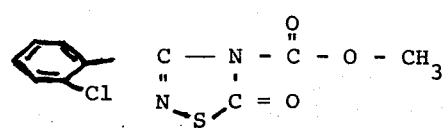

7. A compound of the formula

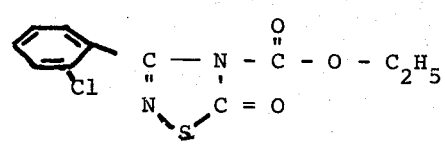

* * * * *

UNITED STATES PATENT AND TRADEMARK OFFICE
CERTIFICATE OF CORRECTION

PATENT NO. : 3,994,909
DATED : November 30, 1976
INVENTOR(S) : Ernst-Heinrich Pommer et al.

It is certified that error appears in the above-identified patent and that said Letters Patent are hereby corrected as shown below:

In The Abstract, delete " ... wherein Z is $-OCH_3$, $-OC_2H_5$, $-OCH(CH_3)NH(CH, -NHC_2H_5$ or $-NH(1H_2)_3CH_3$; "
and substitute
-- ... wherein Z is $-OCH_3$, $-OC_2H_5$, $-OCH(CH_3)_2$, $-NHC_2H_5$ or $-NH(CH_2)_3CH_3$; --

Signed and Sealed this

First Day of November 1977

[SEAL]

Attest:

RUTH C. MASON
*Attesting Officer*

LUTRELLE F. PARKER
*Acting Commissioner of Patents and Trademarks*